US006015558A

United States Patent [19]
Hotamisligil et al.

[11] Patent Number: 6,015,558
[45] Date of Patent: *Jan. 18, 2000

[54] TREATMENT OF INSULIN RESISTANCE IN OBESITY LINKED TYPE II DIABETES USING ANTAGONISTS TO TNF-α FUNCTION

[75] Inventors: Gökhan S. Hotamisligil, Charlestown; Bruce M. Spiegelman, Waban, both of Mass.

[73] Assignee: Dana-Farber Cancer Institute, Inc., Boston, Mass.

[ * ] Notice: This patent is subject to a terminal disclaimer.

[21] Appl. No.: 09/037,777

[22] Filed: Mar. 10, 1998

Related U.S. Application Data

[63] Continuation of application No. 08/255,458, Jun. 8, 1994, Pat. No. 5,730,975, which is a continuation of application No. 07/961,792, Oct. 15, 1992, abandoned.

[51] Int. Cl.$^7$ .................................................. A61K 39/395
[52] U.S. Cl. ................................... 424/142.1; 424/145.1; 424/130.1; 424/158.1
[58] Field of Search .............................. 424/142.1, 85.1, 424/130.1, 141.1, 145.1, 158.1, 192.1, 143.1; 530/350, 388.2, 388.24, 389.2

[56] References Cited

PUBLICATIONS

Ashkenazi, "Protection against endotoxic shock by a tumor necrosis factor receptor immunoadhesin," Proc. Natl. Acad. Sci. USA, 88:10535–10539, Dec. 1991.
Beisel, "Metabolic Response to Infection," Ann. Rev. Med. 26:9 (1975).
Bell, "Molecular Defects in Diabetes Mellitus," Diabetes 40:413 (1990).
Berger et al., "Decreased expression of the insulin–responsive glucose transporter in diabetes and fasting," Nature 340:70 (1989).
Beutler et al., "The Biology of Cachectin/TNF—A Primary Mediator of the Host Response," Ann. Rev. Immunol. 7:625 (1989).
Beutler et al., "Identity of tumour necrosis factor and the macrophage–secreted factor cachetin," Nature 316:552 (1985).
Beutler et al., "Cachectin and tumour necrosis factor as two sides of the same biological coin," Nature 320:584 (1986).
Beutler et al., "Control of Cachectin (Tumor Necrosis Factor) Synthesis: Mechanisms of Endotoxin Resistance," Science 232:977 (1986).
Bjorntorp, "Metabolic Implications of Body Fat Distribution," Diabetes Care 14:1132 (1991).
*Cameron et al., "," Clin. Exp. Pharmacol. Physiol. 5:41 (1978) (Copy not yet available.).
Charron et al., "Divergent Molecular mechanisms for Insulin–resistant Glucose Transport in Muscle and Adipose Cells in Vivo," J. Biol. Chem. 265:7994 (1990).
Choy et al., "Adipsin and an Endogenous Pathway of Complement from Adipose Cells," J. Biol. Chem. 267:1236–12741 (1992).

Coleman et al., "Fat (fat) and Tubby (tub): Two Autosomal Recessive Mutations Causing Obesity Syndrome in the Mouse," J. Heredity 81:424 (1990).
Cook et al., "A developmentally required mRNA from 3T3 adipocytes encodes a novel serine protease homologue," Proc. Natl. Acad. Sci. USA 82:6480 (1985).
Cook et al., "Adipsin: A Circulating Serine Protease Homolog Secreted by Adipose Tissue and Sciatic Nerve," Science 237:402 (1987).
Cornelius et al., "The Growth Factor–like Effects of Tumor Necrosis Factor–α," J. Biol. Chem. 265:20506 (1990).
Dezube et al., "Pentoxifylline and Wellbeing in Patients with Cancer," Lancet, Mar. 17, 1990, p. 662.
Dinarello, "The biology of interleukin 1 and comparison to tumor necrosis factor," Immuno. Lett. 16:227 (1987).
Dohm et al., "Decreased expression of glucose transporter in muscle from insulin–resistant patients," Am. J. Physiol. 260:E459 (1991).
Eriksson, "Increased Incidence of Congenital Malformations in the Offspring of Diabetic Rats and Their Prevention by Maternal Insulin Therapy," Diabetes 31:1 (1982).
Feingold et al., "Tumor Necrosis Factor–Alpha Stimulates Hepatic Lipogenesis in the Rat In Vivo," J. Clin. Invest. 80:184 (1987).
Feingold et al., "Effect of Tumor Necrosis Factor (TNF) on Lipid Metabolism in the Diabetic Rat," J. Clin. Invest. 83:1116 (1989).
Fiers, "Tumor necrosis factor, Characterization at the molecular, cellular and in vivo level," FEBS 285:199 (1991).
Flier et al., "Severely Impaired Adipsin Expression in Genetic and Acquired Obesity," Science 237:405 (1987).
Fraker et al., "Reversal of the toxic effects of cachectin by concurrent insulin administration," Am. J. Physiol. 256:E725 (1989).
Friedman et al., "Tackling a Weighty Problem," Cell 69:217–220 (1992).
Friedman et al., "Restoration of Insulin Responsiveness in Skeletal Muscle of Morbidly Obese Patients after Weight Loss," J. Clin. Invest. 89:701 (1992).

(List continued on next page.)

*Primary Examiner*—Elizabeth Kemmerer
*Assistant Examiner*—Nirmal S. Basi
*Attorney, Agent, or Firm*—Weingarten, Schurgin. Gagnebin & Hayes LLP

[57] ABSTRACT

An induction of TNF-α mRNA expression has been observed in adipose tissue from four different insulin resistant rodent models of obesity and diabetes. TNF-α protein was also elevated locally and systemically. Neutralization of TNF-α in obese fa/fa rats caused a significant increase in the peripheral uptake of glucose in response to insulin. A method of treating an animal suffering from insulin resistance in obesity linked Type II diabetes mellitus is disclosed. The method includes providing a therapeutic agent that includes an antagonist to TNF-α function in a pharmaceutically acceptable carrier substance and administering a pharmacologically effective amount of the therapeutic agent to the animal.

5 Claims, 6 Drawing Sheets

OTHER PUBLICATIONS

Garvey et al., "Gene Expression of GLUT4 in Skeletal Muscle From Insulin–Resistant Patients With obesity, IGT, GDM, and NIDDM," Diabetes 41:465 (1992).

Garvey et al., "Pretranslational Suppression of an Insulin–Responsive Glucose Transporter in Rats with Diabetes Mellitus," Science 245:60 (1989).

Goodwin et al., "Molecular Cloning and Expression of the Type 1 and Type 2 Murine Receptors for Tumor Necrosis Factor," Mol. Cell. Biol. 11:3020 (1991).

Grunfeld et al., "The metabolic effects of tumor necrosis factor and other cytokines," Biotherapy 3:143 (1991).

Grunfeld et al., "Persistence of the Hypertriglyceridemic Effect of Tumor Necrosis Factor Despite Development of Tachyphylaxis to Its Anorectic/Cachectic Effects in Rats," Cancer Res. 49:2554 (1989).

Grunfeld, "Effect of tumor necrosis factor adminstration in vivo on lipoprotein lipase activity in various tissues of the rat," J. Lipid Res. 30:579 (1989).

Handberg et al., "Expression of insulin regulatable glucose transporters in skeletal muscle from Type 2 (non–insulin–dependent) diabetic patients," Diabetologica 33:625 (1990).

Kahn et al., "Differential Regulation of Two Glucose Transporters in Adipose Cells from Diabetic and Insulin–treated Diabetic Rats," J. Clin. Invest. 84:404 (1989).

Kawakami et al., "Lipoprotein lipase suppression in 3T3–L1 cells by an endotoxin–induced mediator from exudate cells," Proc. Natl. Acad. Sci. USA 79:912 (1982).

Kern, "Recombinant human tumor necrosis factor does not inhibit lipoprotein lipase in primary cultures of isolated human adipocytes," J. Lipid Res. 29:909 (1988).

Kettlehut et al., "Tumor Necrosis Factor Can Induce Fever in Rats without Activating Protein Breakdown in Muscle or Lipolysis in Adipose Tissue," J. Clin. Invest. 81:1384 (1988).

Koivisto et al., "Effect of Interferon on Glucose Tolerance and Insulin Sensitivity," Diabetes 38:641 (1989).

Kunkel et al., "Mechanisms That Regulate The Production and Effects of Tumor Necrosis Factor–$\alpha$," Crit. Rev. Immunol. 9:93 (1989).

Lang et al., "Tumor Necrosis Factor Impairs Insulin Action On Peripheral Glucose Disposal And Hepatic Glucose Output," Endocrinology 130:43–52 (1992).

Lardy et al., "Biochemical Aspects of Obesity," Ann. Rev. Biochem. 59:689 (1990).

Le et al., "Biology of Disease," Lab. Invest. 56:234 (1987).

Lewis et al., "Cloning and expression of cDNAs for two distinct murine tumor necrosis factor receptors demonstrate one receptor is species specific," Proc. Natl. Acad. Sci. USA 88:2830 (1991).

Lönnroth, "Regulation of insulin action at the cellular level," J. Intern Med. Suppl. 735:23 (1991).

Mészáros et al., "Tumor Necrosis Factor Increases In Vivo Glucose Utilzation of Macrophage–Rich Tissues," Biochem. Biophys. Res. Comm. 149:1 (1987).

Moller et al., "Insulin Resistance—Mechanisms, Syndromes, and Implications," New Eng. J. Med. 325:938 (1991).

Mullen et al., "Recombinant Tumor Necrosis Factor–$\alpha$ Chronically Administered in Rats: Lack of Cachectic Effect," Proc. Soc. Exp. Biol. Med. 193:318 (1990).

Olefsky et al., "Insulin Resistance in Man," in *Diabetes Mellitus*, H. Rifkin and D. Porte, Jr., eds. (Elsevier Science Publishing Co., Inc., New York, 4th Ed., 1990, pp. 121–153).

Oliff et al., "Tumors Secreting Human TNF/Cachectin Induce Cachexia in Mice," Cell 50:555 (1987).

Olney, "Brain Lesions, Obesity, and Other Disturbancs in Mice Treated with Monosodium Glutamate," Science 164:719 (1969).

Patton et al., "Development of Partial Tolerance to the Gastrointestinal Effects of High Doses of Recombinant Tumor Necrosis Factor–$\alpha$ in Rodents," J. Clin. Invest. 80:1587 (1987).

Pederson et al., "Evidence Against Altered Expression of GLUT1 or GLUT4 in Skeletal Muscle of Patients With Obesity or NIDDM," Diabetes 39:865 (1990).

Pekala et al., "Studies of Insulin Resistance in Adipocytes Induced by Macrophage Mediator," J. Exp. Med. 157:1360 (1983).

Plata–Salaman, "Immunomodulators and Feeding Regulation: A Humoral Link between the Immune and Nervous Systems," Brain Behav. Immun. 3:193 (1989).

Price et al., "Regulation of Lipoprotein Lipase Synthesis by Recombinant Tumor Necrosis Factor—The Primary Regulatory Role of the Hormone in 3T3–L1 Adipocytes," Arch. Biochem. Biophys 251:738 (1986).

Reaven et al., "Role of Abnormal Free Fatty Acid Metabolism in the Development of Non–Insulin–Dependent Diabetes Mellitus," Am. J. Med. 85:106 (1988).

Rey et al., "Interleukin 1 affects glucose homeostatis," Am. J. Physiol. 253:R794 (1987).

Ron et al., "Tumor Necrosis Factor–induced Reversal of Adipoxytic Phenotype of 3T3–L1 cells Is Preceeded by a Loss of Nuclear CCAAT/Enhancer Binding Protein (C/EBP)," J. Clin. Invest. 89:223 (1992).

Rosen et al., "Adipsin and Complement Factor D Activity: An Immune–Related Defect in Obesity," Science 244:1483 (1989).

Semb et al., "Multiple Effects of Tumor Necrosis Factor on Lipoprotein Lipase in Vivo," J. Biol. Chem. 262:8390 (1987).

Shafrir, "Diabetes in Animals," in *Diabetes Mellitus*, H. Rifkin and D. Porte, Jr., eds. (Elsevier Science Publishing Co., Inc., New York, 4th Ed., 1990, pp. 299–340).

Sherman et al., "Recombinant Human Tumor Necrosis Factor Administered as a Five–Day Continuous Infusion in Cancer Patients: Phase I Toxicity and Effect on Lipid Metabolism" J. Clin. Oncol. 6:344 (1988).

Sinha et al., "Adipose Tissue Glucose Transporters in NIDDM," Diabetes 40:472 (1991).

Sivitz et al., "Regulation of glucose transporter messenger RNA in insulin–deficient states," Nature 340:72 (1989).

Socher et al., "Recombinant Human Tumor Necrosis Factor Induces Acute Reductions in Food Intake and Body Weight in Mice," J. Exp. Med. 167:1957 (1988).

Stephens et al., "Differential Regulation of glucose Transporter Gene Expression in Adipose Tissue of Septic Rats," Biochem. Biophys. Res. Comm. 183:417 (1992).

Stephens et al., "Transcriptional Repression of the GLUT4 and C/EBP Genes in 3T3–L1 Adipocytes by Tumor Necrosis Factor–$\alpha$," J. Biol. Chem. 266:21839 (1991).

Strieter et al., "Cellular and Molecular Regulation of Tumor Necrosis Factor–Alpha Production by Pentoxifylline," Biochem. biophys. Res. Comm. 155:1230–1236 (1988).

Tartaglia et al., "The two different receptors for tumor necrosis factor mediate distinct cellular responses," Proc. Natl. Acad. Sci. USA 88:9292 (1991).

Teng et al., "Long–term inhibition of tumor growth by tumor necrosis factor in the absence of cachexia or T–cell immunity," Proc. Natl. Acad. Sci. USA 88:3535 (1991).

Torti et al., "A Macrophage Factor Inhibits Adipocyte Gene Expression: An in Vitro Model of Cachexia," Science 229:867 (1985).

Tracey et al., "Metabolic Effects of Cachectin/Tumor Necrosis Factor Are Modified by Site of Production," J. Clin. Invest. 86:2014 (1990).

Truett et al., "Rat obesity gene fatty (fa) maps to chromosome 5: Evidence for homology with the mouse gene diabetes (db)," Proc. Natl. Acad. Sci. USA 88:7806 (1991).

Van Snick, "Interleukin–6: An Overview," Ann. Rev. Immunol. 8:253 (1990).

Heidrich et al., "Blood Glucose and Serum Insulin Levels Following Acute and Chronic Pentoxifyline Administration," Acta Diabetologica Latina 17:15–21 (1980).

Raptis et al., "24–H Glucose Pattern in Type I and Type II Diabetics After Oral Treatment with Pentoxifylline as Assessed by Artificial Endocrine Pancreas," Acta Diabetologica Latina 24:181–192 (1987).

Ambrus et al., "Effect fo Pentoxigylline on Carbohydrate Metabolism . . . ", Archives of Internal Medicine 150:921, Apr., 1990.

Hotamisligil et al., "Adipose Expression of Tumor Necrosis Factor–alpha . . . ", Science 259:87–91, Jan., 1993.

Spiegelman et al., "Regulation of Adipocyte Gene Expression in Differentiation . . . ", J. of Biological Chem. 268:6823–6826, Apr., 1993.

Spiegelman et al., "Through Thick and Thin: Wasting, Obesity, and TNF alpha.", Cell 73:625–627.

Rodger, W., "Non–insulin–dependent (type II) Diabetes Mellitus", Canadian Medical Assoc. Journal 145:1571–1581, Dec., 1991.

TREATMENT OF INSULIN RESISTANCE IN OBESITY LINKED TYPE II DIABETES USING ANTAGONISTS TO TNF-α FUNCTION

CROSS-REFERENCES TO RELATED APPLICATIONS

This application is a continuation of application Ser. No. 08/255,458, filed Jun. 8, 1994, U.S. Pat. No. 5,730,975, which was a continuation of now-abandoned application Ser. No. 961,792, filed Oct. 15, 1992.

STATEMENT REGARDING FEDERALLY SPONSORED RESEARCH

This invention was supported by an NIH grant, DK42539.

BACKGROUND OF THE INVENTION

Obesity and diabetes are among the most common human health problems in industrialized societies. Obesity, which is the result of an imbalance between caloric intake and energy expenditure, is highly correlated with insulin resistance and diabetes in experimental animals and humans. However, the molecular mechanisms that are involved in obesity-diabetes syndromes are not clear. Since adipose tissue is the major site for energy storage and mobilization, many investigators have focused on finding abnormalities in adipocyte physiology or metabolism (Plata-Salaman, Brain Behav. Immun. 3:193, 1989; Lardy et al., Annu. Rev. Biochem. 59:689, 1990).

It has been shown that several cytokines such as tumor necrosis factor (TNF)-α have direct effects on adipocyte metabolism as well as other important metabolic actions (Le et al., Lab. Invest. 56:234, 1987; Dinarello, Immunol. Lett. 16:227, 1987; Kunkel et al., Crit. Rev. Immunol. 9:93, 1989; Grunfeld et al., Biotherapy 3:143, 1991). TNF-α acts in vitro on murine adipocytes to suppress expression of most adipose specific genes including enzymes involved in lipogenesis (Kawakami et al., Proc. Natl. Acad. Sci. USA 79:912, 1982; Price et al., Arch. Biochem. Biophys. 251:738, 1986). However, some of these effects are not observed in primary cultures of human or rat adipocytes (Grunfeld et al., Biotherapy 3:143, 1991; Kern, J. Lipid Res. 29:909, 1988).

In vivo, TNF-α expression has been associated with catabolic states leading to a "wasting syndrome," termed cachexia (Beutler et al., Nature 316:552, 1985; Beutler et al., Science 232:977, 1986; Beutler et al., Nature 320:584, 1986; Oliff et al., Cell 50:555, 1987; Beutler et al., Ann. Rev. Immunol. 7:625, 1989), but this effect of TNF-α has been challenged by several groups of investigators (Semb et al., J. Biol. Chem. 262:8390, 1987; Grunfeld et al., J. Lipid Res. 30:579, 1989; Feingold et al., J. Clin. Invest. 83:1116, 1989; Patton et al., J. Clin. Invest. 80:1587 (1987); Kettlehut et al., J. Clin. Invest. 81:1384, 1988; Tracey et al., J. Clin. Invest. 86:2014, 1990; Socher et al., J. Exp. Med. 167:1957, 1988; Mullen et al., Proc. Soc. Exp. Biol. Med. 193:318, 1990; Teng et al., Proc. Natl. Acad. Sci. USA 88:3535, 1991; for reviews see C. Grunfeld et al., Cancer Res. 49:2554, 1989; Fiers, FEBS 285:199, 1991).

TNF-α administration causes an increase in serum triglycerides and very low density lipoproteins in rats and humans (Semb et al., J. Biol. Chem. 262:8390, 1987; Grunfeld et al., J. Lipid Res. 30:579, 1989; Feingold et al., J. Clin. Invest. 83:1116, 1989; Sherman et al., J. Clin. Oncol. 6:344, 1988). This hyperlipidemia is thought to be the result of decreased lipoprotein lipase activity and increased hepatic lipogenesis (Feingold et al., J. Clin. Invest. 80:184, 1987). TNF-α administration also has effects on appetite and gastrointestinal tract functions (Plata-Salaman, Brain Behav. Immun. 3:193, 1989). Besides TNF-α, other cytokines such as TNF-β, IL-1, IL-6 and interferon (INF) also have profound effects on lipid metabolism (Grunfeld et al., Biotherapy 3:143, 1991). Furthermore, all of these cytokines affect glucose homeostasis in various tissues (Rey et al., Am. J. Physiol. 253:R794, 1987; Meszaros et al., Biochem. Biophys. Res. Comm. 149:1, 1987; Koivisto et al., Diabetes 38:641, 1989; Snick, Annu. Rev. Immunol. 8:253, 1990).

Previous studies have also suggested an association of TNF-α with states of peripheral insulin resistance, especially in infection. First, it is established that biological mediator(s) generated during infection interfere with insulin's actions and lead to profound metabolic alterations (Beutler et al., Ann. Rev. Immunol. 7:625, 1989; Stephens et al., J. Biol. Chem. 266:21839, 1991; Beisel, Ann. Rev. Med. 26:9, 1975; Stephens et al., Biochem. Bioph. Res Common. 183:417, 1992). Second, incorporation of glucose into lipids is decreased upon short term treatment of 3T3-L1 cells with supernatants of activated macrophages (Olney, Science 164:719, 1969; Cameron et al., Cli. Exp. Pharmacol. Physiol. 5:41, 1978), and third, treatment of L6 myotubes (Cornelius et al., J. Biol. Chem. 265:20506, 1990) and 3T3-L1 adipocytes with recombinant TNF-α causes downregulation of Glut4 expression (Stephens et al., J. Biol. Chem. 266:21839, 1991). However, the specificity of TNF-α's effect on Glut4 mRNA in fat cells was not clear in that expression of many or most other fat cell genes was also affected (Stephens et al., J. Biol. Chem. 266:21839, 1991). Finally, a recent study has directly demonstrated that chronic, low level administration of TNF-α to rodents induces systemic insulin resistance (Lang et al., Endocrinology 130:43, 1992).

Insulin resistance, defined as a smaller than expected biological response to a given dose of insulin, is a ubiquitous correlate of obesity. Indeed, many of the pathological consequences of obesity are thought to involve insulin resistance. These include hypertension, hyperlipidemia and, most notably, non-insulin dependent diabetes mellitus (NIDDM). Most NIDDM patients are obese, and a very central and early component in the development of NIDDM is insulin resistance (reviewed in Moller et al., New Eng. J. Med. 325:938, 1991). It has been demonstrated that a post-receptor abnormality develops during the course of insulin resistance, in addition to the insulin receptor downregulation during the initial phases of this disease (Olefsky et al., in *Diabetes Mellitus*, H. Rifkin and D. Porte, Jr., Eds. (Elsevier Science Publishing Co., Inc., New York, ed. 4, 1990), pp. 121–153). Several studies on glucose transport systems as potential sites for such a post-receptor defect have demonstrated that both the quantity and function of the insulin sensitive glucose transporter (Glut4) is deficient in insulin resistant states of rodents and humans (Garvey et al., Science 245:60, 1989; Sivitz et al., Nature 340:72, 1989; Berger et al., Nature 340:70, 1989; Kahn et al., J. Clin. Invest. 84:404, 1989; Charron et al., J. Biol. Chem. 265:7994, 1990; Dohm et al., Am. J. Physiol. 260:E459, 1991; Sinha et al., Diabetes 40:472, 1991; Friedman et al., J. Clin. Invest. 89:701, 1992). A lack of a normal pool of insulin-sensitive glucose transporters could theoretically render an individual insulin resistant (Olefsky et al., in *Diabetes Mellitus*, H. Rifkin and D. Porte, Jr., Eds. (Elsevier Science Publishing Co., Inc., New York, ed. 4, 1990), pp. 121–153). However, some studies have failed to show downregulation of Glut4 in human NIDDM, especially in muscle, the major site of glucose disposal (for a review see G. I. Bell, Diabetes 40:413, 1990; Pederson et al., Diabetes 39:865, 1990; Handberg et al., Diabetologia 33:625, 1990; Garvey et al., Diabetes 41:465, 1992).

The mechanistic link between obesity and insulin resistance is not understood. Much attention has been focused on the role of free fatty acids as potential mediators of insulin resistance (Reaven et al., Am. J. Med. 85:106, 1988; Lonnroth, J. Intern. Med. Suppl. 735:23, 1991; Bjorntorp, Diabetes Care 14:1132, 1991). Free fatty acid levels are typically elevated in obesity, and fatty acids have been shown to affect insulin sensitivity in vitro and in vivo (Reaven et al., Am. J. Med. 85:106, 1988; Lonnroth, J. Intern. Med. Suppl. 735:23, 1991; Bjorntorp, Diabetes Care 14:1132, 1991).

SUMMARY OF THE INVENTION

It has surprisingly been shown that an induction of TNF-α mRNA expression can be observed in adipose tissue from four different insulin resistant rodent models of obesity and diabetes. TNF-α protein is also elevated locally and systemically. Neutralization of TNF-α in obese fa/fa rats with an antagonist to TNF-α function causes a significant increase in the peripheral uptake of glucose in response to insulin, thus overcoming inherent insulin resistance.

Thus, the invention generally features a method of treating an animal suffering from insulin resistance in obesity linked Type II diabetes mellitus. The method includes providing a therapeutic agent that includes an antagonist to TNF-α function and a pharmaceutically acceptable carrier substance and administering to the animal a pharmacologically effective amount of the therapeutic agent.

Preferably, the therapeutic agent includes as antagonist to TNF-α function a receptor, most preferably a TNF-α receptor or effective portion thereof; a monoclonal antibody, most preferably an anti-TNF-α monoclonal antibody or effective portion thereof; or an agent capable of suppressing production of TNF-α or of TNF-α mRNA, most preferably pentoxifylline. Additionally, the agent preferably includes immunoglobulin, most preferably in a chimeric complex with the antagonist to TNF-α function.

As used herein the term "antagonist to TNF-α function" includes any agent that interacts with TNF-α and interferes with its function, e.g., antibody or portions thereof reactive with TNF-α, the TNF-α receptor or portions thereof reactive with TNF-α, or any other ligand which binds to TNF-α. The term also includes any agent that will interfere in the overproduction of TNF-α mRNA or TNF-α protein or antagonize one or both TNF-α receptors. Such agents may be in the form of chimeric hybrids, useful for combining the function of the agent with a carrier protein to increase the serum half-life of the therapeutic agent or to confer cross-species tolerance.

Other features and advantages of the invention will be found in the following description of the preferred embodiments thereof and in the claims.

DESCRIPTION OF THE PREFERRED EMBODIMENTS

The discovery that TNF-α expression is elevated in rodent models of obesity and diabetes has permitted the development of a therapeutic treatment for overcoming the insulin resistance associated with obesity linked Type II diabetes mellitus. Described below are experiments that led to this discovery.

Figure 1:
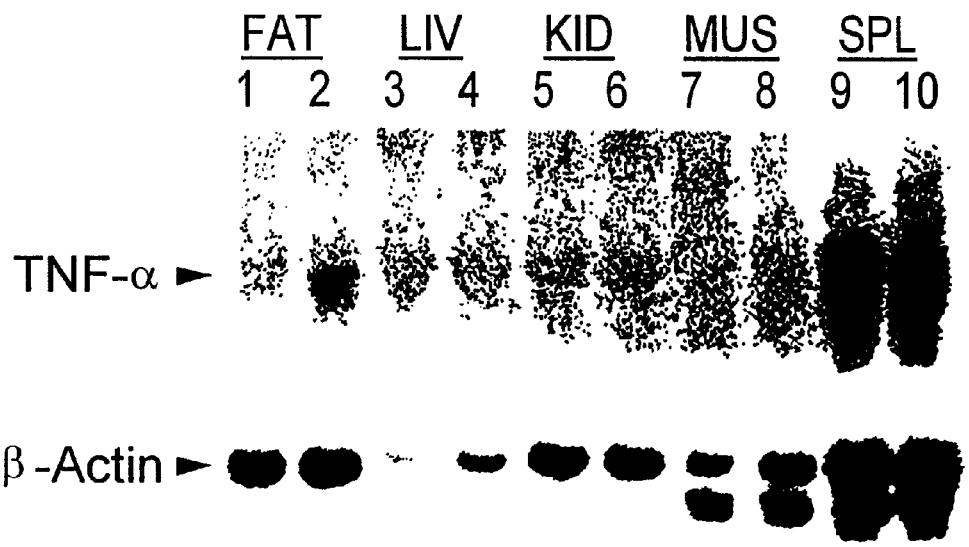
FIG. 1 shows endogenous expression of the TNF-α gene in various tissues or organs of lean or obese mice compared to the expression of β-actin.

To examine the expression of the TNF-α gene in the tissues of lean (+/?) or obese (db/db) mice, total RNA was extracted from various tissues and organs and subjected to RNA (Northern blot) analysis (FIG. 1). Endogenous expression was evident only in adipose tissue and spleen. The level of TNF-α mRNA expression in spleen was not different in obese mice compared to their lean litter mates. However, in adipose tissue the amount of TNF-α mRNA per unit of RNA was at least 5–10 fold elevated in obese animals compared to lean controls. TNF-β, IL-1-α and -β and IL-6 were neither expressed in fat tissue nor regulated in obesity in any other organ. The earliest time of adipose expression of TNF-α examined was 6–7 weeks of age in db/db mice and 3–4 weeks of age in fa/fa rats, when animals are known to be obese and insulin resistant, but not significantly hyperglycemic (Coleman, Diabetes 31:1, 1982; Shafrir, in *Diabetes Mellitus;* H. Rifkin and D. Porte, Jr. Eds. (Elsevier Science Publishing Co., Inc., New York, ed. 4, 1990), pp. 299–340). TNF-α mRNA in fat tissue was elevated at these times.

Figure 2:
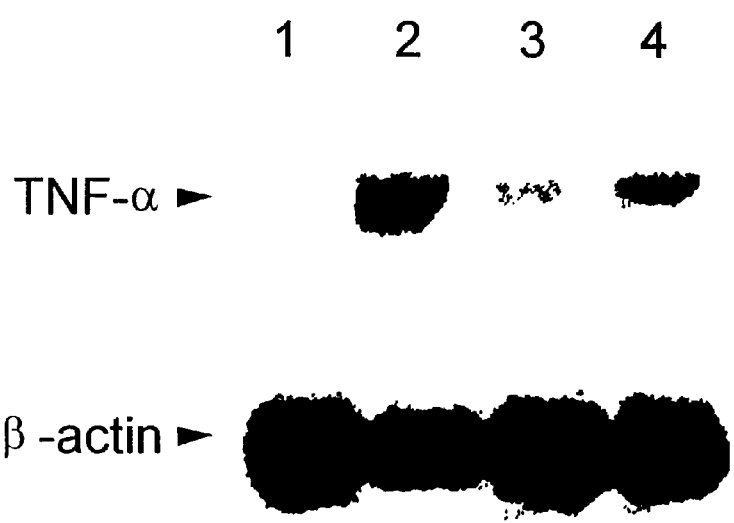
FIG. 2 shows the source of TNF-α expression in adipose tissue.

Adipose tissue consists of vascular endothelial cells, smooth muscle cells, fibroblasts, local mast cells and macrophages besides adipocytes (Wasserman, in *Handbook of Physiology,* A. E. Renold and G. F. Cahill, Eds. (Am. Physiol. Soc., Washington D.C., 1965), vol. 5, pp. 87–100). To determine the source of TNF-α expression in adipose tissue, mature adipocytes and non-adipose cells (stromal-vascular fraction) were separated as described (Rodbell, J. Biol. Chem. 239:375, 1964), and the amount of mRNA associated with these compartments was determined. The majority of the TNF-α mRNA fractionated with the adipocytes although some was also detected in the stromal-vascular fraction that contains non-adipocytes plus less mature adipocytes (FIG. 2). These results suggest that adipocytes express TNF-α mRNA in vivo and are the major source of the elevated levels of mRNA expression in adipose tissue.

Figure 3:
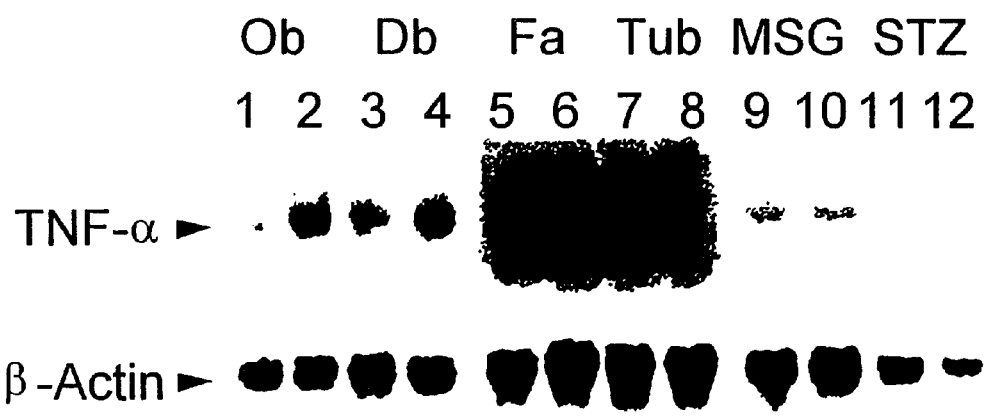
FIG. 3 shows adipose TNF-α expression in different rodent models of genetic and chemically induced obesity or diabetes.

As metabolic profiles differ among various animal models of obesity and diabetes, analysis of multiple models was undertaken to separate the effects of hyperinsulinemia, hyperglycemia and obesity. The diabetes (db/db) and obese (ob/ob) mice are characterized by massive obesity, hyperphagia, variable hyperglycemia, insulin resistance, hyperinsulinemia and impaired thermogenesis (Coleman, Diabetes 31:1, 1982; E. Shafrir, in *Diabetes Mellitus;* H. Rifkin and D. Porte, Jr. Eds. (Elsevier Science Publishing Co., Inc., New York, ed. 4, 1990), pp. 299–340). However, diabetes is much more severe in the db/db model (Coleman, Diabetes 31:1, 1982; E. Shafrir, in *Diabetes Mellitus;* H. Rifkin and D. Porte, Jr. Eds. (Elsevier Science Publishing Co., Inc., New York, ed. 4, 1990), pp. 299–340). Zucker (fa/fa) rats are severely obese, hyperinsulinemic, and insulin resistant (Coleman, Diabetes 31:1, 1982; E. Shafrir, in *Diabetes Mellitus;* H. Rifkin and D. Porte, Jr. Eds. (Elsevier Science Publishing Co., Inc., New York, ed. 4, 1990), pp. 299–340), and the fa/fa mutation may be the rat equivalent of the murine db mutation (Friedman et al., Cell 69:217–220, 1992; Truett et al., Proc. Natl. Acad. Sci. USA 88:7806, 1991). Tubby (tub/tub) mice are characterized by obesity, moderate insulin resistance and hyperinsulinemia without significant hyperglycemia (Coleman et al., J. Heredity 81:424, 1990). Like the db/db mouse, the ob/ob, tub/tub and fa/fa models exhibit a similar obesity related expression of TNF-α mRNA in fat (FIG. 3).

The monosodium glutamate (MSG) model for chemically-induced obesity (Olney, Science 164:719, 1969; Cameron et al., Cli. Exp. Pharmacol. Physiol. 5:41, 1978), in which obesity is less severe than in the genetic models and develops without hyperphagia, hyperinsulinemia and insulin resistance, was also examined. No induction of TNF-α mRNA in MSG-treated animals was observed (FIG. 3). Finally, the streptozotocin (STZ) model for chemically-induced diabetes was tested to examine the effects of hyperglycemia in the absence of obesity. STZ-treated animals are deficient in insulin and severely hyperglycemic (Coleman, Diabetes 31:1, 1982; E. Shafrir, in *Diabetes Mellitus;* H. Rifkin and D. Porte, Jr. Eds. (Elsevier Science Publishing Co., Inc., New York, ed. 4, 1990), pp. 299–340). STZ-treated rats did not exhibit induction of TNF-α expression in fat tissue. These results suggest that TNF-α induction is best correlated with severe obesity and insulin resistance. Detection of elevated TNF-α gene expression in four independent animal models suggests that this may be a general phenomenon in these disorders.

The differences in mRNA levels in the adipose tissues of lean and obese animals are also reflected in the amounts of local and systemic (circulating) TNF-α protein. Local protein production was examined in explanted adipose tissue, and a significant amount of TNF-α secretion was observed. When expressed as the mass of TNF-α secreted per unit of tissue DNA, the obese adipose tissue secreted approximately twice as much TNF-α as the lean tissue. The levels of TNF-α in circulation were determined by the ELISA assay in plasma of 24 control and db/db animals. Only 6/24 (25%) lean animals had detectable levels of TNF-α protein, with levels ranging from 25 to 97.7 pg/ml (61.53±11.9). In obese animals TNF-α protein was detectable in 14/24 (58.3%), with levels ranging from 34 to 165.6 pg/ml (85.6±10.0). These differences in the fraction of lean or obese animals having detectable TNF-α levels in the plasma were statistically significant with a p value <0.05, indicating that TNF-α protein in circulation is also elevated in obese animals. However, the circulating protein concentrations detected in plasma were quite low.

Figure 4:
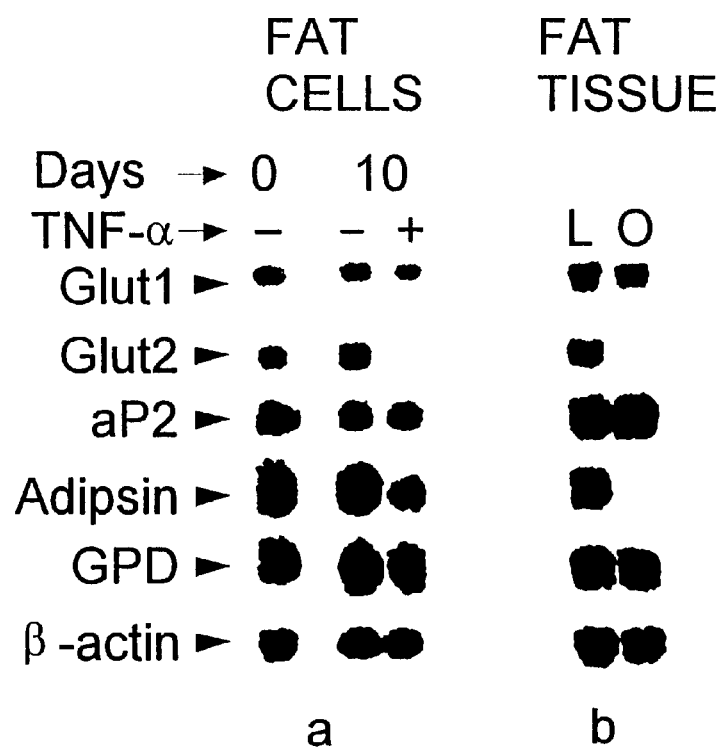
FIG. 4a shows the pattern of specific mRNA expression in cultured murine fat cells upon low dose TNF-α treatment.
FIG. 4b shows the pattern of specific mRNA expression in adipose tissue in obese animals upon low dose TNF-α treatment.

Most studies examining the effects of TNF-α on adipocytes have reported a general suppression of fat cell gene expression and, in some cases, a dedifferentiation response (Torti et al., Science 229:867, 1985; Pekala et al., J. Exp. Med. 157:1360, 1983; Ron et al., J. Clin. Invest. 89:223, 1992; Cornelius et al., J. Biol. Chem. 265:20506, 1990; Stephens et al., J. Biol. Chem. 266:21839, 1991). However, the interpretation of most of these studies is complicated by the fact that very high doses of mixed cytokines or human TNF-α were often used, and it is now known that recombinant human TNF-α binds only to one of the two murine TNF receptors (Lewis et al., Proc. Natl. Acad. Sci. USA 88:2830, 1991). Because of the results presented above, we have examined the chronic effects (10–15 days) of low dose (50 pM; 2 ng/ml) murine TNF-α treatment on cultured murine fat cells. This treatment did not cause any phenotypic changes in 3T3-F442A adipocytes. We then examined the pattern of specific mRNA, especially that for adipsin and Glut4, the insulin-sensitive glucose transporter that is expressed in muscle and fat. Both of these genes are expressed in a differentiation-dependent manner in adipocytes and are specifically downregulated in obesity-insulin resistance syndromes (Flier et al., Science 237:405, 1987; Rosen et al., Science 244:1483, 1989; Choy et al., J. Biol. Chem. 267:12736–12741, 1992; Garvey et al., Science 245:60, 1989; Sivitz et al., Nature 340:72, 1989; Berger et al., Nature 340:70, 1989; Kahn et al., J. Clin. Invest. 84:404, 1989; Charron et al.,. J. Biol. Chem. 265:7994, 1990; Dohm et al., Am. J. Physiol. 260:E459, 1991; Sinha et al., Diabetes 40:472, 1991; Friedman et al., J. Clin. Invest. 89:701, 1992). Long term treatment of adipocytes with TNF-α led to downregulation of Glut4 mRNA (FIG. 4*a*). This down regulation is not general for most fat specific genes as no changes were observed in the mRNA levels for the fatty acid binding protein aP2, and glycerophosphate dehydrogenase (GPD). Glut1 and β-actin mRNA were also unaffected. However, a dramatic reduction in adipsin mRNA was evident (FIG. 4*a*). The gene expression pattern of these cells is strikingly similar to that of adipose tissue in obese animals (FIG. 4*b*) where Glut4 and adipsin mRNA expression are also severely deficient but most other fat specific genes are expressed fairly normally (Flier et al., Science 237:405, 1987; Rosen et al., Science 244:1483, 1989; Choy et al., J. Biol. Chem. 267:12736–12741, 1992). These results strongly suggest that TNF-α could be a key mediator of abnormal gene expression in obesity-diabetes syndromes and may affect glucose homeostasis.

To use the results of the above studies in developing a treatment regimen for insulin resistance, a neutralization of TNF-α in vivo was undertaken and its effect on glucose homeostasis of genetically obese and insulin resistant animals examined. For neutralization, a recombinant soluble TNF-α receptor-IgG chimeric protein (TNFR-IgG, Genentech, Inc., San Francisco, Calif.) was used (Ashkenazi et al., Proc. Natl. Acad. Sci. USA 88:10535, 1992). This molecule was administered iv into fa/fa rats daily, for 3 days (200 μg/rat), and a steady blood level of 47.69±4.79 ng/ml was established (Ashkenazi et al., Proc. Natl. Acad. Sci. USA 88:10535, 1992; plasma TNFR-IgG assays were done by ELISA (Bender Medsystems, Vienna, Austria). In vivo insulin sensitivity was then examined by utilizing two-step hyperinsulinemic-euglycemic clamps according to the following protocol.

Upon arrival, Zucker obese rats (fa/fa) were housed for at least a week prior to experimental procedures. Surgeries for the placement of jugular vein and carotid artery catheters were performed under sterile conditions using ketamine and xylazine (i.m.) anesthesia. After surgery, all rats were allowed to regain consciousness and placed in individual cages. TNFR-IgG (200 μg/rat in 200 μl volume) or vehicle (20% glycerol in PBS; 200 μl/rat) was administered through the jugular vein after complete recovery and for the following two days. Sixteen hours after the last treatment, hyperinsulinemic-euglycemic clamps were performed. Rats were placed in restrainers and a bolus of 4 μCi [3-$^3$H] glucose (NEN) was administered, followed by a continuous infusion of the tracer at a dose of 0.2 μCi/min (20 μl/min). Two hours after the start of the tracer infusion, 3 blood samples (0.3 ml each) were collected at 10 minute intervals (-20-0 min) for basal measurements. An insulin infusion was then started (5 mU/kg/min), and 100 μl blood samples were taken every 10 min. to monitor plasma glucose. A 30% glucose solution was infused using a second pump based on the plasma glucose levels in order to reach and maintain euglycemia. Once a steady state was established at 5 mU/kg/min insulin (stable glucose infusion rate and plasma glucose), 3 additional blood samples (0.3 ml each) were obtained for measurements of glucose, [3-$^3$H] glucose and insulin (100–120 min.). A higher dose of insulin (25 mU/kg/min.) was then administered and glucose infusion rates were adjusted for the second euglycemic clamp and blood samples were taken at min. 220–240. Glucose specific activity was determined in deproteinized plasma and the calculations of Rd and HGO were made, as described (Lang et al., Endocrinology 130:43, 1992). Plasma insulin levels at basal period and after 5 and 25 mU/kg/min. infusions were 102.6±9.4, 188.4±41.4 and 667.4±76.0 ng/ml in controls and 95.46±12.4, 200.5±23.6 and 659.1±39.7 ng/ml in TNFR-IgG-treated animals.

In summary, plasma insulin levels following 2 doses of constant insulin infusion (5 mU and 25 mU/kg/min) were similar in control and TNFR-IgG-treated animals. Plasma glucose levels (FIG. 5a) and glucose infusion rates to maintain euglycemia under hyperinsulinemia (FIG. 5b) were stable in both groups of animals during the clamps. However, at all time points and at the two different insulin doses, TNFR-IgG-treated animals required 2–3 times more glucose to maintain normal blood glucose levels, indicating a greater response to insulin.

Figure 6A:
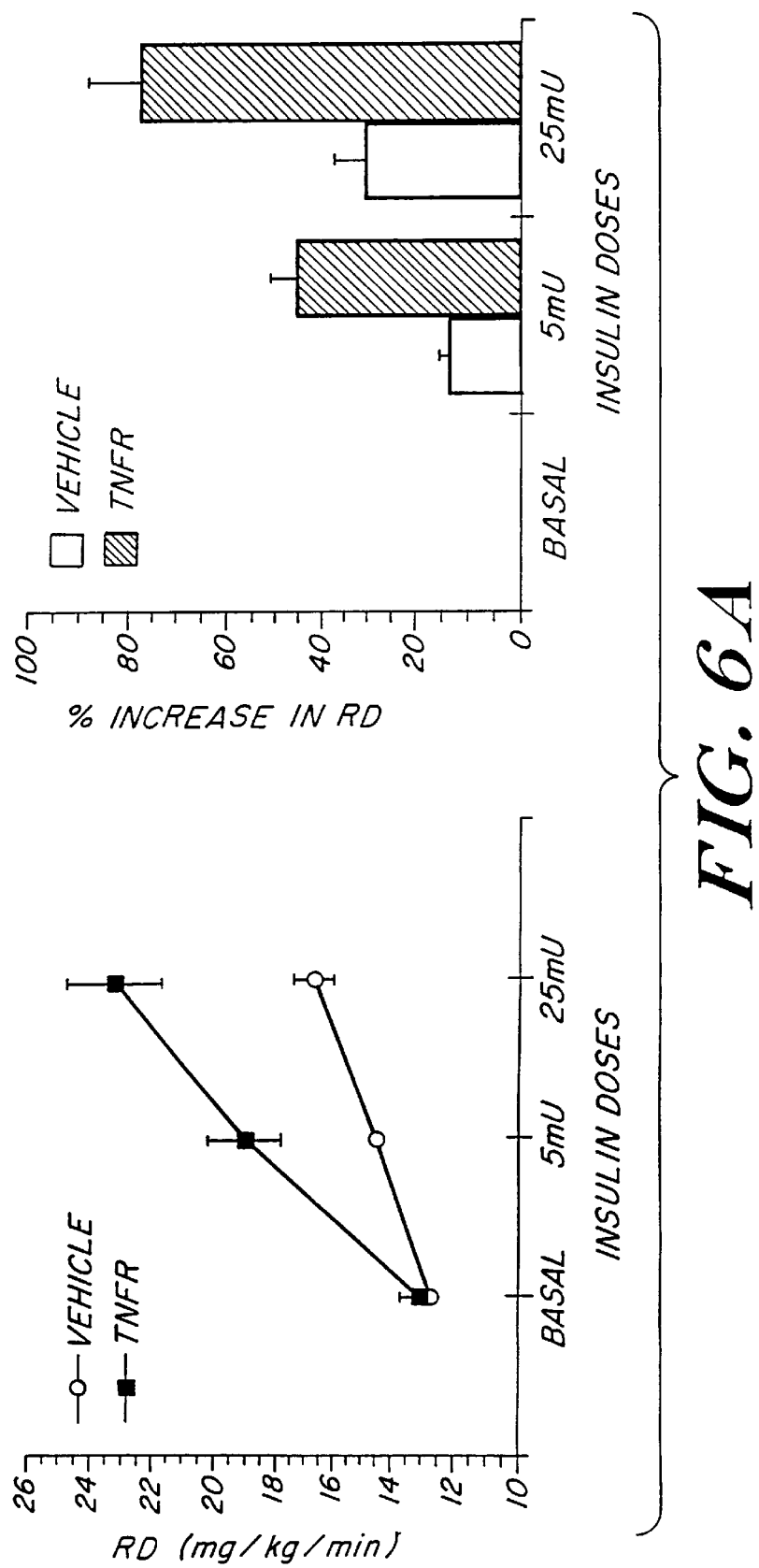
FIG. 6a shows increase in insulin-stimulated peripheral glucose utilization rate (Rd) in control and TNFR-IgG-treated animals.
Figure 6B:
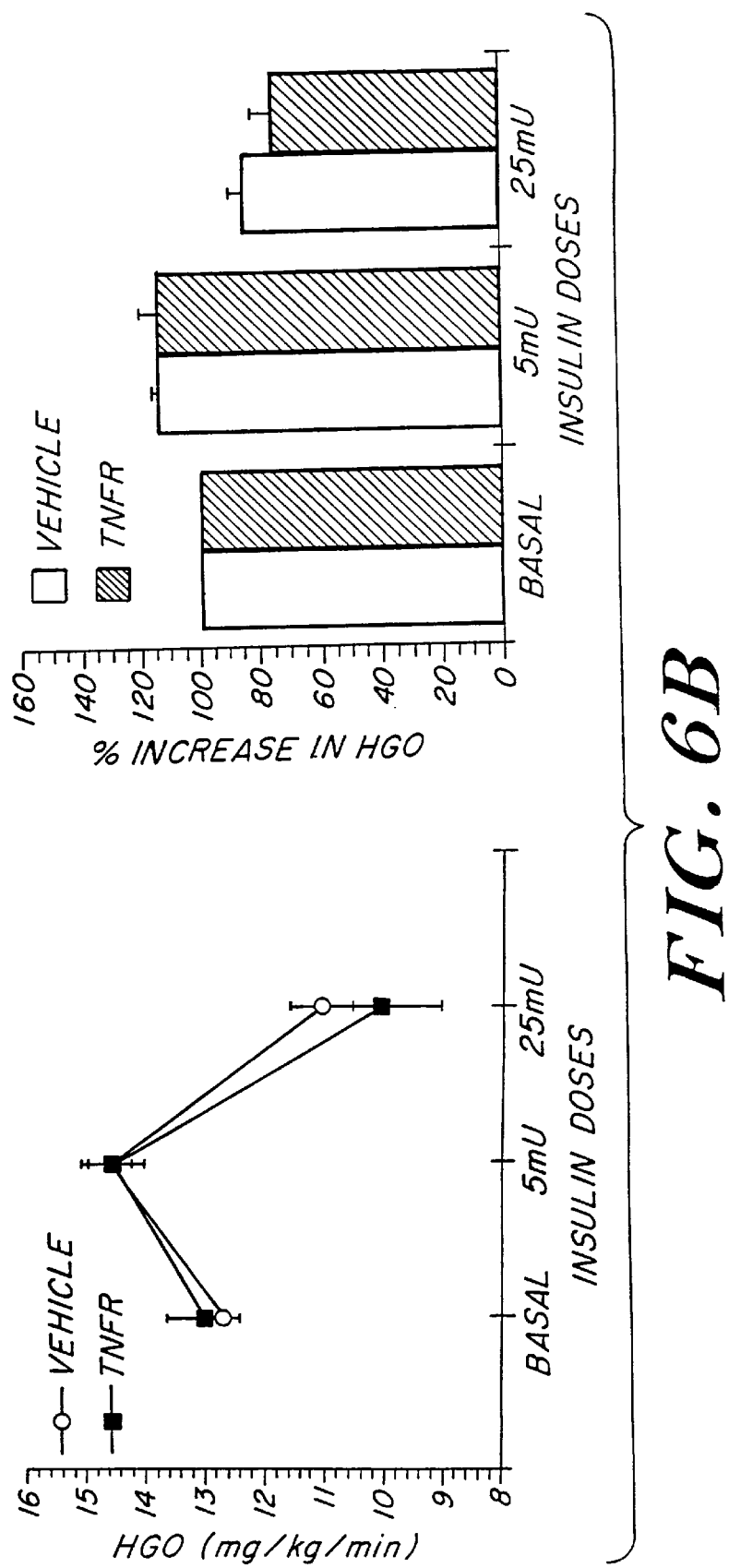
FIG. 6b shows hepatic glucose output (HGO) in control and TNFR-IgG-treated animals.

Insulin regulation of glucose homeostasis has two major components; stimulation of peripheral glucose uptake and suppression of hepatic glucose output. Using tracer studies in the glucose clamps, it was possible to determine which portion of the insulin response was affected by the soluble receptor. As illustrated in FIG. 6a, insulin-stimulated peripheral glucose utilization rate (Rd) was 2–3 fold higher in the TNFR-IgG-treated animals while hepatic glucose output (HGO) was unaffected (FIG. 6b). Thus, the neutralization of TNF-α has profound effects on the sensitivity to insulin in obese-diabetic animals. This effect is predominantly seen as increased peripheral glucose uptake.

Not being bound by any theory, one must still address the question of how a putative role for TNF-α in obesity-linked insulin resistance can be reconciled with its possible role in cachexia (Beutler et al., Nature 316:552, 1985, Beutler et al., Science 232:997, 1986; Beutler et al., Nature 320:584, 1986, Oliff et al., Cell 50:555, 1987). Clearly, this appears to be a question of the hormonal milieu of the organism and the relative levels of this cytokine (Fraker et al., Am. J. Physiol. 256:E725, 1989). The levels produced in the obese rodents or those that yield insulin resistance when given exogenously (Lang et al., Endocrinology 130:43, 1992) are far lower than those which can induce a variety of other symptoms, including cachexia (Beutler et al., Nature 316:552, 1985; Beutler et al., A. Cerami., Science 232:977, 1986; Beutler et al., Nature 320:584, 1986; Oliff et al., Cell 50:555, 1987). These dose dependent differences in biological effects are especially in accord with recent data demonstrating at least two different receptor systems, having different affinities for TNF-α (Lewis et al., Proc. Natl. Acad. Sci. USA 88:2830, 1991; Goodwin et al., Mol. Cell Biol. 11:3020, 1991; Tartaglia et al., Proc. Natl. Acad. Sci. USA 88:9292. 1991).

Materials and Methods

Expression of TNF-α mRNA in the Tissues of Lean and Obese Mice

Total RNA from tissues of 7–8 week old, male, lean (+/?) and obese (db/db) animals (Jackson Laboratories, Bar Harbor, Me.), were extracted by a cesium chloride extraction protocol (Chirgwin et al., Biochemistry 18:5294, 1979). Total RNA (20 μg) was denatured in formamide and formaldehyde at 55° C. for 15 min. and separated by electrophoresis in formaldehyde-containing agarose gels, as described (Maniatis et al., Molecular Cloning: A Laboratory Manual Cold Spring Harbor Laboratory, Cold Spring Harbor, N.Y., ed. 2, 1989). RNA was blotted onto Biotrans membranes, UV-crosslinked (Stratagene) and baked for 0.5 hours. Hybridization and washes were done as directed by the manufacturer. DNA probes were radioactively labeled to specific activities of at least $10^9$ d.p.m./μg with [$^{32}$P]-α-dCTP (6000 Ci/mmol) by the random priming method (Maniatis et al., Molecular Cloning: A Laboratory Manual Cold Spring Harbor Laboratory, Cold Spring Harbor, N.Y., ed. 2, 1989). Referring to FIG. 1, lanes 1 and 2 show epididymal fat, lanes 3 and 4 show liver, lanes 5 and 6 show kidney, lanes 7 and 8 show skeletal muscle, and lanes 9 and 10 show spleen. Odd numbered lanes show lean mice and even numbered lanes show obese. β-actin mRNA is shown as a control for loading and integrity of the RNA. Lean mice are designated as +/? since +/+ and db/+ animals have not been differentiated.

TNF-α mRNA Expression in Cell-fractionated Adipose Tissue

Epididymal fat pads were isolated from 12–13 week old, male lean (+/?) and obese (db/db) mice, washed in sterile PBS, minced, washed with Krebs-Ringer bicarbonate (KRB) buffer (pH 7.4) containing 4% albumin and 5 mM glucose, and treated with collagenase (0.5 mg/ml) on a shaking platform at 37° C. for 30 min. (Rodbell, J. Biol. Chem. 239:375, 1964). The incubation medium was filtered through Nitex screen filters (250 μm pore size) to remove undigested tissue. Adipocytes were then separated by their ability to float upon low speed centrifugation. To obtain total stromalvascular fractions, the medium below the adipocyte layer was centrifuged at 200× g for 10 minutes and the pellets were washed 3× with warm KRB buffer. Total RNA was extracted from fractions as described above. Referring to FIG. 2, lanes 1 and 2 show adipocyte fraction, and lanes 3 and 4 show stromal-vascular fraction. Odd numbered lanes show lean mice and even numbered lanes show obese. β-actin mRNA is shown as a control for loading and integrity of RNA.

Adipose Expression of TNF-α mRNA in Different Rodent Models of Genetic and Chemically Induced Obesity or Diabetes Total RNA (20 μg) from epididymal fat pads of different animal models was determined. The ob/ob, db/db and tub/tub obese mice and their lean controls were obtained from Jackson Laboratories (Bar Harbor, Me.), and Zucker rat tissues were from Drs. F. Gregoire and M. R. C. Greenwood (University of California at Davis). For monosodium glutamate (MSG) treatment, 3 mg per gram body weight MSG was subcutaneously injected into neonatal mice and tissues were collected 7 weeks later. These mice were a gift from Dr. S. Ross (University of Illinois Medical School). Streptozotocin-treated rats (0.1 mg per g body weight streptozotocin (STZ) was intraperitoneally injected into 5–6 week old rats and tissues were collected 8 days later) were from Dr. R. C. Kahn (Joslin Diabetes Center, Boston, Mass.). The cDNA clone for murine TNF-α, a gift of Dr. Bruce Beutier (University of Texas, Southwestern Medical Center), was subjected to Northern blot analysis as described above. Referring to FIG. 3, lane 1 shows +/? lean mice, lane 2 shows ob/ob obese mice, lane 3 shows +/? lean mice, lane 4 shows db/db obese mice, lane 5 shows +/? lean rat, lane 6 shows fa/fa obese rat, lane 7 shows tub/+ lean mice, lane 8 shows tub/tub obese mice, lane 9 shows Swiss-Webster lean mice, lane 10 shows MSG-treated Swiss-Webster obese mice, lane 11 shows Wistar non-diabetic rat, and lane 12 shows STZ-treated Wistar diabetic rat. All animals were males; +/?, ob/ob, +/?, db/db, tub/+ and tub/tub mice were 12–13 weeks old; and +/? and fa/fa rats were 7–8 weeks old. β-actin mRNA is shown as a control for loading and integrity of the RNA.

Effect of Chronic Treatment of 3T3-F442A Cells With Murine TNF-α on Adipocyte Gene Expression Referring to FIG. 4a, murine 3T3-F442A adipocytes were cultured and differentiated in 10% fetal calf serum and 5 μg/ml insulin, as described (Dobson et al., J. Biol. Chem. 262:1804, 1987; Choy et al., J. Biol. Chem. 267:12736–12741, 1992). Adipocyte conversion was essentially complete by seven days post-confluence. Day 0 represents the time when cells were fully differentiated. Adipocytes were then treated with 50 pM recombinant murine TNF-α (Genzyme Corporation, Cambridge, Mass.) for 10 days in the same medium. Total RNA was extracted from adipocytes, as described (Dobson et al., J. Biol. Chem. 262:1804, 1987; Choy et al., J. Biol. Chem. 267:12736–12741, 1992) and subjected to Northern blot analysis and probed with cDNAs for glucose transporter type 1 (Glut1), glucose transporter type 4 (Glut4), fatty acid binding protein aP2, adipsin/complement factor D, glycerophosphate dehydrogenase (GPD) and β-actin. Referring to FIG. 4b, total RNA (20 μg) from epididymal fat pads of 12–13 week old, male, +/? lean (L), and db/db obese (O) animals were subjected to Northern blot analysis and probed with the same markers as described above.

Glucose Control During Hyperinsulinemic-euglycemic Clamps

Figure 5A:
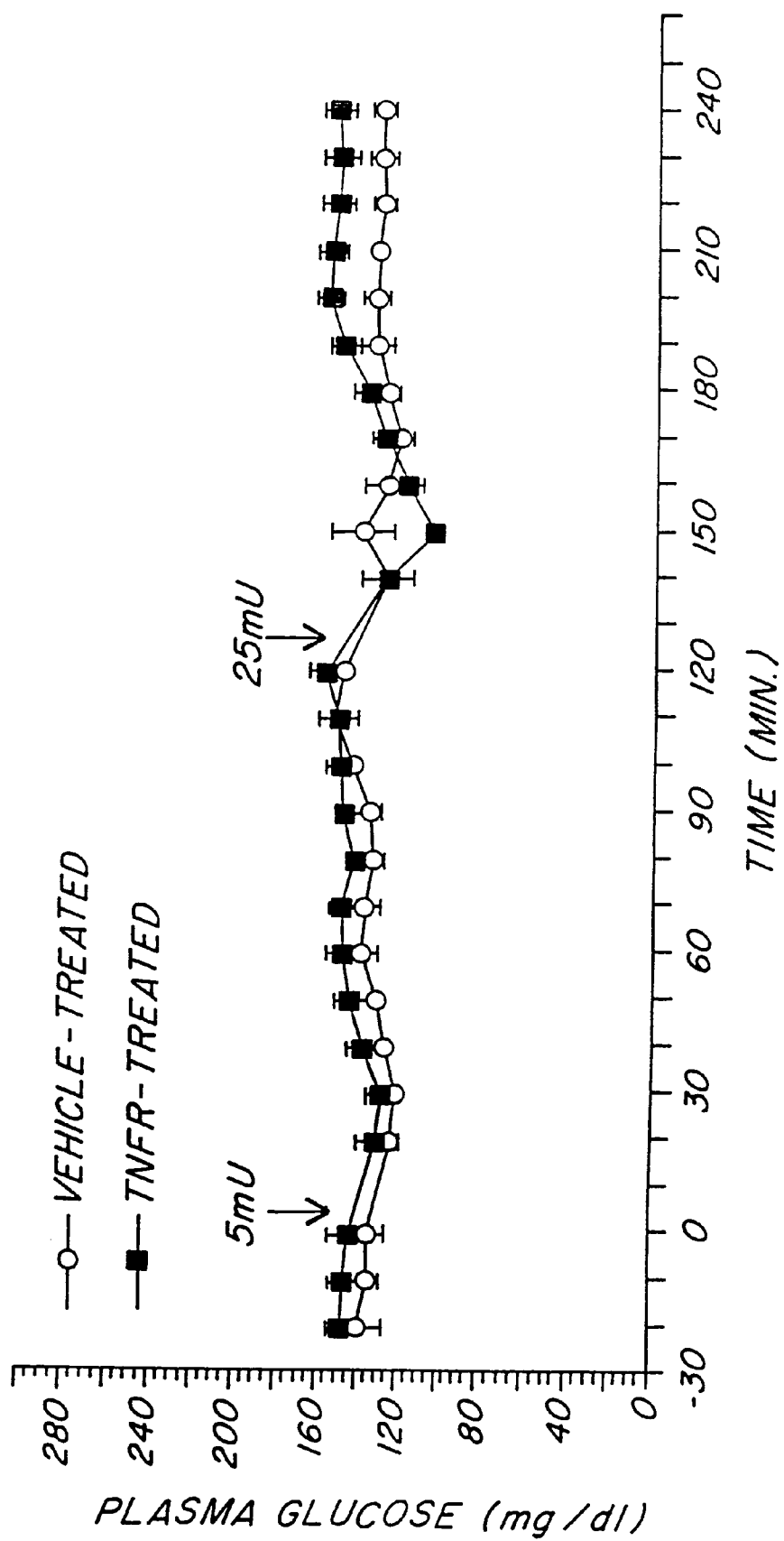
FIG. 5a shows plasma glucose levels over time in control and TNFR-IgG-treated animals.
Figure 5B:
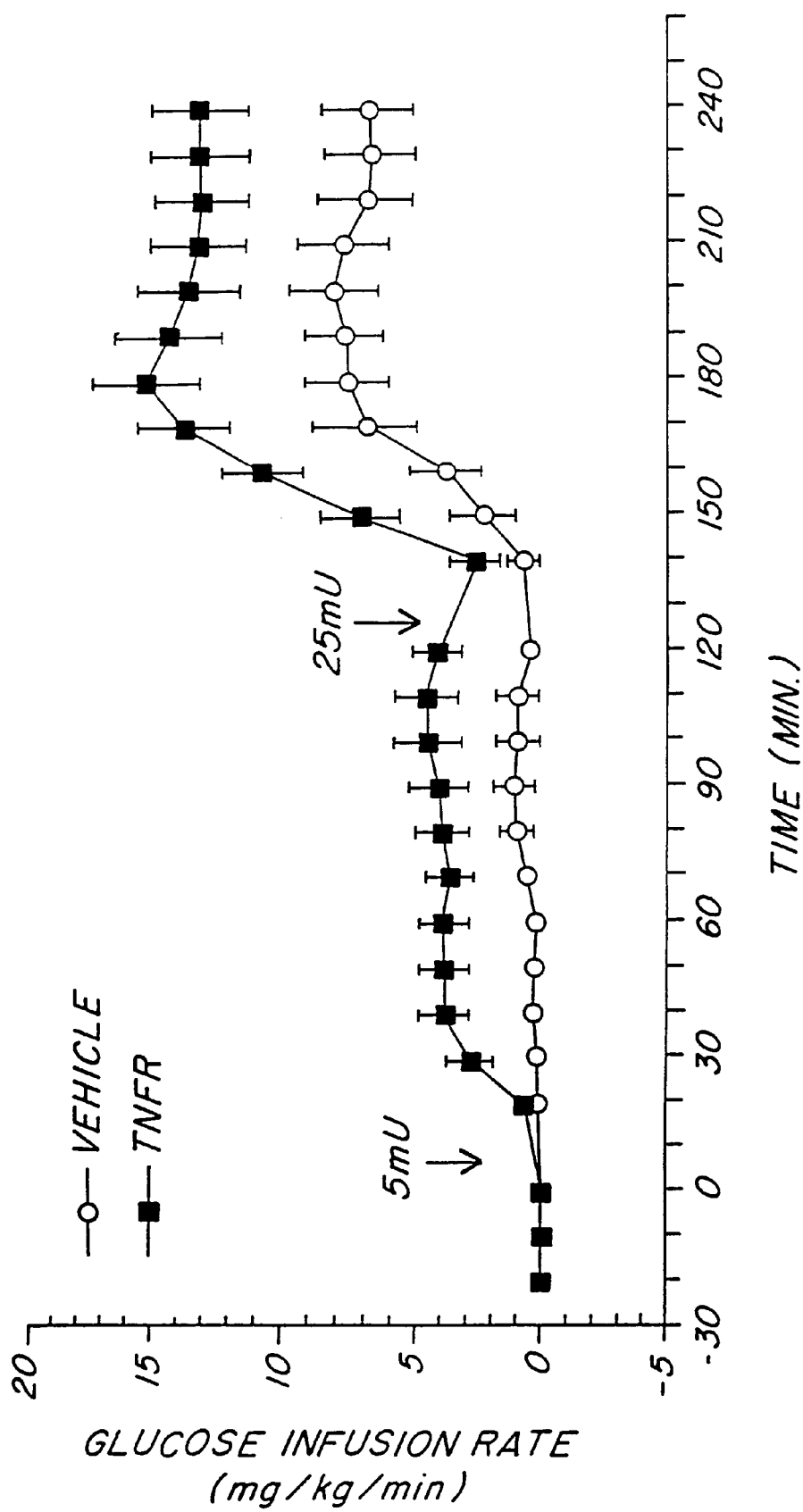
FIG. 5b shows glucose infusion rates to maintain euglycemia under hyperinsulinemia over time in control and TNFR-IgG-treated animals.

FIG. 5a shows plasma glucose levels, and FIG. 5b shows glucose infusion rates. Male, 7–9 weeks old, fa/fa rats (Charles River Laboratories, Mass.) were intravenously treated with 200 μg/rat TNFR-IgG (n=8) or vehicle (20% glycerol in PBS) (n=5) for 3 consecutive days, and ~16 hours after the last treatment, glucose clamps were performed on conscious animals (34). The values represent the mean ±SE of plasma glucose and glucose infusion rates of all animals within each group at a given time point.

Effect of TNFR-IgG Infusion on Glucose Homeostasis in fa/fa Rats

Peripheral glucose utilization (Rd) and hepatic glucose uptake (HGO) were calculated, as described ((34); Beisel, Ann. Rev. Med. 26:9, 1975; Stephens et al., Biochem. Bioph. Res. Comm. 183:417, 1992). Rd increased 45.65 and 78.26% over basal upon 5 and 25 mU/kg/min insulin infusion, respectively, in TNFR-IgG-treated animals. The same doses of insulin infusions resulted in 13.84 and 31.02% increase over basal in controls. FIG. 6a shows peripheral glucose utilization, and FIG. 6b shows hepatic glucose output. The values represent the mean ±SE of Rd and HGO of all animals in each group.

Use

The TNF-α receptor, anti-TNF-α monoclonal antibodies, or individual portions thereof can be used for therapeutic treatment to interfere with TNF-α binding either at the ligand or receptor level and reduce insulin resistance. In addition, any of the specific antagonists can be joined to a carrier protein to increase the serum half-life of the therapeutic agent. For example, a soluble immunoglobulin chimera such as described herein, can be obtained for each specific TNF-α antagonist or antagonistic portion thereof, as described in Capon et al., U.S. Pat. No. 5,116,964, the whole of which is hereby incorporated by reference herein. The immunoglobulin chimera are easily purified through IgG-binding protein A-Sepharose chromatography. The chimera have the ability to form an immunoglobulin-like dimer with the concomitant higher avidity and serum half-life.

Additionally, the therapeutic agent may be a molecule capable of suppressing production of TNF-α or of TNF-α mRNA. As shown by Strieter et al. in "Cellular and Molecular Regulation of Tumor Necrosis Factor-Alpha Production by Pentoxifylline" (Biochem. Biophys. Res. Commun. 155:1230, 1988, the whole of which is hereby incorporated by reference herein), pentoxifylline is able to suppress the production of both biologically active TNF-α and TNF-α mRNA expression by more than 50%.

A candidate antagonist can be assayed for effectiveness, e.g., via the hyperinsulinemic-euglycemic clamp technique as described herein. Alternatively, the effect of the candidate agent on reducing circulating levels of TNF-α can be measured in an ELISA assay. Agents believed to function by interacting with one or both TNF-α receptors can be examined for their effect on fat cell gene expression as described herein.

The therapeutic agents may be administered orally, topically, or parenterally, (e.g., intranasally, subcutaneously, intramuscularly, intravenously, or intra-arterially) by routine methods in pharmaceutically acceptable inert carrier substances. Optimal dosage and modes of administration can readily be determined by conventional protocols. Preferably, administration would be systemic and a decrease in insulin resistance would be manifested in a drop in circulating levels of glucose and/or insulin in the patient.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A method of treating an animal suffering from insulin resistance, said method comprising administering to said animal a therapeutic agent that is effective in decreasing insulin resistance, said agent comprising an antagonist to TNF-α function in a pharmaceutically acceptable carrier substance, said agent causing an increase in the peripheral uptake of glucose in response to insulin, wherein said agent comprises an antibody or a portion thereof that interferes with binding of TNF-α to a TNF receptor or that suppresses production of TNF-α protein or of TNF-α m-RNA.

2. The method of claim 1 wherein said therapeutic agent comprises a monoclonal antibody.

3. The method of claim 1, wherein said therapeutic agent comprises an anti-TNF-α monoclonal antibody or portion thereof that interferes with binding of TNF-α to a TNF-α receptor.

4. The method of claim 1 wherein said insulin resistance is further associated with obesity.

5. The method of claim 1 wherein said insulin resistance is further associated with Type II diabetes mellitus.

* * * * *